United States Patent
Nunes et al.

(10) Patent No.: US 11,925,329 B2
(45) Date of Patent: Mar. 12, 2024

(54) METHODS AND SYSTEMS FOR ADJUSTING BEHAVIOR OF PERSONAL CARE DEVICE BASED ON STATUS OF ORAL CAVITY

(71) Applicant: KONINKLIJKE PHILIPS N.V., Eindhoven (NL)

(72) Inventors: Dionisio Massingo Nunes, Utrecht (NL); Vincent Jeanne, Migne Auxances (FR); Wilhelmus Johannes Everardus Evers, Eindhoven (NL); Felipe Maia Masculo, Eindhoven (NL); Martin John Edwards, Solihull (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 714 days.

(21) Appl. No.: 17/053,120

(22) PCT Filed: May 10, 2019

(86) PCT No.: PCT/EP2019/062024
§ 371 (c)(1),
(2) Date: Nov. 5, 2020

(87) PCT Pub. No.: WO2019/215318
PCT Pub. Date: Nov. 14, 2019

(65) Prior Publication Data
US 2021/0068528 A1    Mar. 11, 2021

Related U.S. Application Data (60) Provisional application No. 62/669,587, filed on May 10, 2018.

(51) Int. Cl.
*A46B 15/00*    (2006.01)
*A61B 1/24*     (2006.01)
(Continued)

(52) U.S. Cl.
CPC .............. *A61B 1/24* (2013.01); *A61B 5/7267* (2013.01); *A61C 17/221* (2013.01); *G06N 20/00* (2019.01);
(Continued)

(58) Field of Classification Search
None
See application file for complete search history.

(56) References Cited

U.S. PATENT DOCUMENTS

| | | | |
|---|---|---|---|
| 8,031,175 B2 | 10/2011 | Rigazio | |
| 9,724,179 B2 | 8/2017 | Simeth | |

(Continued)

FOREIGN PATENT DOCUMENTS

| | | |
|---|---|---|
| CN | 204463125 U | 7/2015 |
| CN | 106806032 A | 6/2017 |

(Continued)

OTHER PUBLICATIONS

International Search Report and Written Opinion, International Application No. PCT/EP2019/062024, dated Jul. 15, 2019.

*Primary Examiner* — K. Wong (57) ABSTRACT

A personal care device including at least one sensor (28) configured to obtain sensor data including information about a user; a controller (30) having a feature extraction module (230) and a classifier (240), the feature extraction module configured to extract one or more features from the obtained sensor data, the classifier configured to determine a status of a user based on the extracted one or more features; and a personal care device (10) configured to provide a personal care function and receive one or more control signals to adjust the personal care function based on a determined status of at least a portion of the user's body.

20 Claims, 5 Drawing Sheets

(51) Int. Cl.
  *A61B 5/00* (2006.01)
  *A61C 17/22* (2006.01)
  *G06N 20/00* (2019.01)
(52) U.S. Cl.
  CPC ....... *A46B 15/0004* (2013.01); *A46B 15/0016* (2013.01); *A46B 2200/1066* (2013.01)

(56) References Cited

U.S. PATENT DOCUMENTS

| | | | |
|---|---|---|---|
| 10,646,029 B2* | 5/2020 | Serval | A61B 5/486 |
| 10,702,191 B2* | 7/2020 | Vetter | A46B 15/0006 |
| 10,702,206 B2* | 7/2020 | Vetter | A61B 5/0002 |
| 11,337,756 B2* | 5/2022 | Allison | A61B 5/01 |
| 2004/0106081 A1 | 6/2004 | Karazivan et al. | |
| 2004/0260234 A1 | 12/2004 | Srinivasan et al. | |
| 2008/0060148 A1 | 3/2008 | Pinyayev et al. | |
| 2009/0262073 A1 | 10/2009 | Rigazio et al. | |
| 2011/0143310 A1 | 6/2011 | Hunter | |
| 2011/0294089 A1 | 12/2011 | Karazivan et al. | |
| 2012/0246846 A1* | 10/2012 | Hall | A46B 15/0004 15/21.1 |
| 2015/0223743 A1 | 8/2015 | Pathangay | |
| 2017/0020277 A1 | 1/2017 | Barnes et al. | |
| 2021/0393026 A1* | 12/2021 | Subhash | A61C 17/3481 |

FOREIGN PATENT DOCUMENTS

| | | |
|---|---|---|
| CN | 107028674 A | 8/2017 |
| WO | 2013001462 A2 | 1/2013 |

* cited by examiner

METHODS AND SYSTEMS FOR ADJUSTING BEHAVIOR OF PERSONAL CARE DEVICE BASED ON STATUS OF ORAL CAVITY

CROSS-REFERENCE TO RELATED APPLICATIONS

This application is the U.S. National Phase application under 35 U.S.C. § 371 of International Application No. PCT/EP2019/062024, filed on 10 May 2019, which claims the benefit of U.S. Provisional Application No. 62/669,587, filed 10 May 2018. These applications are hereby incorporated by reference herein.

FIELD OF THE INVENTION

The present disclosure is directed generally to methods and systems for adjusting behavior of a personal care device based on a status of an oral cavity.

BACKGROUND

Powered oral care devices, such as, toothbrushes and interdental cleaners are operated in environments where the substances with which the powered oral care devices come into contact are desired to be contained. Toothpaste, saliva, and blood are example substances that can be unintentionally expelled from the mouth during use of a powered oral care device.

In addition, oral care devices including imaging sensors that image the oral cavity are used, for example, in teledentistry to obtain dental images requested by a dental professional. However, since the individual operating the device cannot easily visualize the screen of the imaging device while positioning the device to collect the requested content, the quality of the images obtained and the efficiency of the process of obtaining the images suffer.

Accordingly, there is a continued need in the art for methods and systems for constraining the flight of oral fluids into the environment to provide a more disease-free environment and improve overall user experience. There is also a continued need in the art for methods and systems for improving the quality of oral images obtained from imaging sensors on oral care devices.

SUMMARY OF THE INVENTION

The present disclosure is directed to inventive personal care systems and methods for controlling a powered personal care device based on a status of an oral cavity. A personal care system may include one or more sensors configured to sense changes in and around a user's body, an algorithm to infer a state of the user's body, and a personal care device configured to provide one or more personal care functions for a user (e.g., brushing, flossing, oral irrigation, imaging, etc.). The personal care device is also configured to automatically adjust the one or more personal care functions in response to a transmitted control signal based on the status of the user's oral cavity determined by a controller. For example, the inventive systems and methods enable identification of whether a user's mouth is open, closed, opening, or closing, and allow for the automatic adjusting of one or more personal care functions of the powered personal care device based on the status of the user's mouth.

Generally, in one aspect, a personal care system is provided. The personal care system includes at least one sensor configured to obtain sensor data including information about the body of a user and a controller having a feature extraction module and a classifier, the feature extraction module configured to extract one or more features from the obtained sensor data, and the classifier configured to determine a status of the oral cavity based on the extracted one or more features. The personal care system also includes a personal care device configured to i) provide a personal care function and ii) receive one or more control signals to adjust the personal care function based on a determined status of the oral cavity.

In one embodiment, the personal care system includes a device function engine configured to receive a control signal from the controller and transmit one or more control signals to the personal care device to adjust the personal care function.

In various embodiments, the personal care device is a powered toothbrush or an interdental cleaner.

In various embodiments, the at least one sensor is an imaging sensor or an optical proximity sensor.

Generally, in another aspect, a method for controlling a personal care device based on a status of a user's oral cavity is provided. The method includes providing a personal care function with a personal care device; obtaining, by one or more sensors associated with the personal care device, sensor data including information about an oral cavity of a user; extracting, by a feature extraction module, one or more features from the obtained sensor data; determining a state of the oral cavity based on the extracted one or more features; and based on the determined state of the oral cavity, transmitting one or more control signals to adjust the personal care function provided by the personal care device.

In one embodiment, the method further includes training a classifier using the extracted one or more features to create a classification model to predict the state of the oral cavity prior to the determining step.

In one embodiment, the step of determining the state of the oral cavity includes assigning a weight to the sensor data from each of the one or more sensors.

In one embodiment, the step of determining the state of the oral cavity further includes applying a normalization function to the weighted sensor data from each of the one or more sensors.

In one embodiment, the method further includes the step of providing feedback to the user or a third party based on the determined state of the oral cavity.

In various embodiments, the personal care device is a powered toothbrush and the personal care function is a brushing intensity or a brushing mode.

In one embodiment, the personal care function is a powered or non-powered state.

In one embodiment, the personal care device is an imaging device and the one or more sensors include an imaging sensor and the personal care function is capturing an image of the oral cavity.

As used herein for purposes of the present disclosure, the term "controller" is used generally to describe various apparatus relating to the operation of a personal care device, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of systems and methods for automatically adjusting one or more functions of a powered personal care device based on a status of the user's mouth to improve overall user experience. More generally, Applicant has recognized and appreciated that it would be beneficial to provide a system and method for identifying or characterizing a status of a user's oral cavity and controlling a powered personal care device based on the status of the user's oral cavity. Accordingly, the methods and systems described or otherwise envisioned herein provide one or more sensors capable of sensing changes in and around a user's mouth, an algorithm to infer a status of the user's mouth based on changes in sensor signals, and a powered personal care device that can be electronically controlled or adjusted during use.

A particular goal of utilization of certain embodiments of the present disclosure is to automatically modify a brushing mode or brushing intensity or turn a personal care device on or off when a user's mouth is open, opening, closing, or closed. Another particular goal of utilization of certain embodiments of the present disclosure is to automatically capture images of a user's oral cavity when a user's mouth is sufficiently open.

The embodiments and implementations disclosed or otherwise envisioned herein can be utilized with any suitable powered personal care device. Examples of suitable personal care devices include an electric toothbrush, a shaver, a flossing device, an oral irrigator, a tongue cleaner, a skin care device, or other personal care device. However, the disclosure is not limited to these personal care devices, and thus the disclosure and embodiments disclosed herein can encompass any handheld or personal care device.

Figure 1:
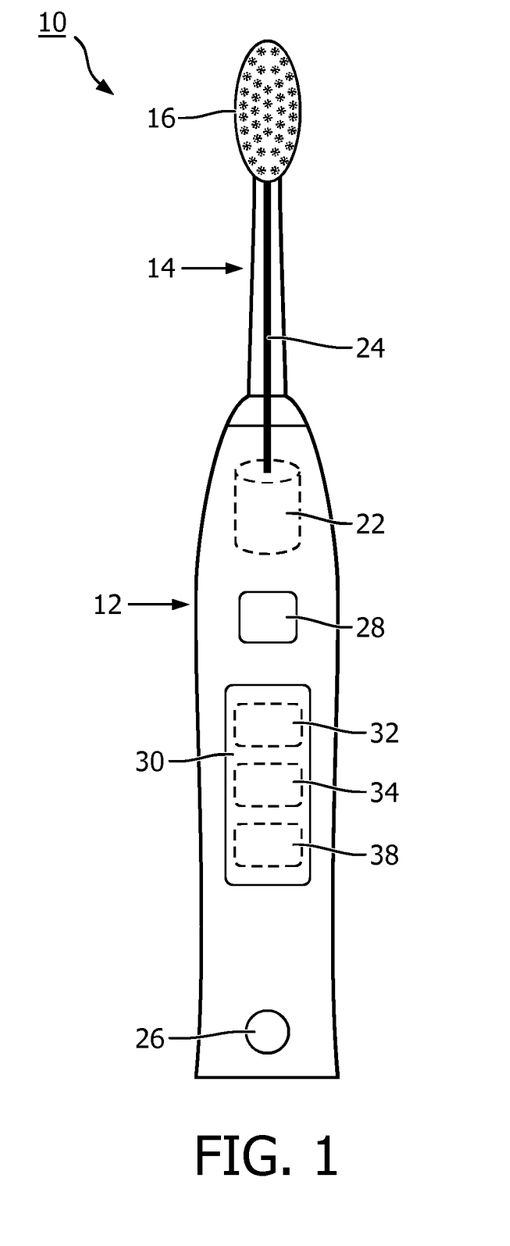
FIG. 1 is a schematic representation of an oral care device, in accordance with an embodiment.

Referring to FIG. 1, in one embodiment, a personal care device 10 is provided that includes a handle or body portion 12 and a head member 14. Head member 14 includes at its end remote from the body portion an operating component 16. The body portion 12 typically includes a housing, at least a portion of which is hollow, to contain components of the personal care device. The body portion 12 can include a drivetrain assembly with a motor 22 for generating movement, and a transmission component or drivetrain shaft 24, for transmitting the generated movements to head member 14.

According to one embodiment, head member 14 is mounted to the drivetrain shaft 24 so as to be able to move relative to body portion 12. The movement can be any of a variety of different movements, including vibrations or rotation, among others. For example, the head member 14 can be fixedly mounted onto drivetrain shaft 24, or it may alternatively be detachably mounted so that head member 14 can be replaced with a different head member for different operating features, or when components of the head member are worn out and require replacement. Although in the present embodiment the powered personal care device 10 shown in FIG. 1 is an electric toothbrush, it will be understood that the personal care device can be any other powered personal care device.

Body portion 12 is further provided with a user input 26 to allow a user to operate the powered personal care device 10, for example, to turn the device on and off. The user input 26 may, for example, be a button, touch screen, or switch.

Powered personal care device 10 includes one or more sensors 28 configured to obtain sensor data indicative of changes in and/or around a user's body during use of the personal care device 10. Sensor 28 is shown in FIG. 1 within body portion 12, but may be located anywhere within the device, including, for example, within head member 14, operating component 16, or elsewhere within or on the device. According to an embodiment, sensor 28 can include one or more optical proximity sensors, pressure sensors, and/or other sensor modalities whose output is sensitive to the state of the user's body, or parts thereof.

Figure 2:
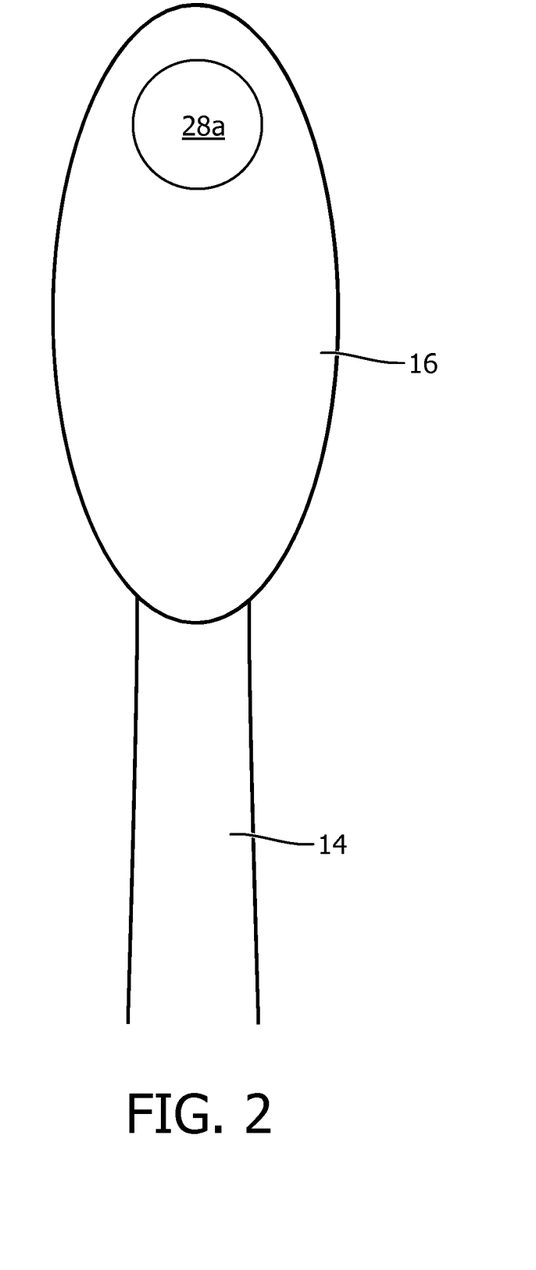
FIG. 2 is a schematic representation of a head of an oral care device, in accordance with an embodiment.

Referring to FIG. 2, in an embodiment, personal care device 10 includes one or more sensors 28 that are an imaging sensor 28a to obtain images of a user's body, or the relevant portions thereof. Imaging sensor 28a can be any imager capable of obtaining images, preferably in a digital format, for example, a CCD or CMOS sensor. In alternate embodiments, imaging sensor 28a can be a standalone digital camera, or a camera integrated into a smartphone, a smart mirror, a wearable computing device, and/or any other computing device. The imaging device or imager may include or otherwise be in communication with a light source configured to illuminate one or more regions of the user's body. For example, the light source may be a flash or other light source associated with the device. The light source can be or include any light source, such as an LED light source, that emits light capable of facilitating high-quality imaging. According to an embodiment, the light source includes light from two or more light sources. The imager and/or light source may be configured to operate periodically, continuously, and/or in response to a stimulus. For example, the imager and light source can obtain an image in response to a user taking an image, in response to a user positioning the imager over a portion of the body, as detected by the imager in real-time, or in response to a user positioning the imager within or near a specific region of the body, such as if the imager is on an oral care device positioned within the oral cavity when it is sufficiently open or opening, as detected by the system as described herein.

The personal care device 10 further includes a controller 30 configured to receive sensor data generated by one or more sensors 28. According to one embodiment, sensor 28 is integral to controller 30. Controller 30 may be formed of one or multiple modules, and is configured to operate the powered personal care device 10 in response to an input, such as input obtained via user input 26 and/or a status of the user's body as detected by one or more sensors 28. Controller 30 can include, for example, a processor 32 and a memory 34 or similar database. Processor 32 may take any suitable form, including but not limited to a microcontroller, multiple microcontrollers, circuitry, a single processor, or plural processors. Memory or database 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of personal care device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

Figure 3:
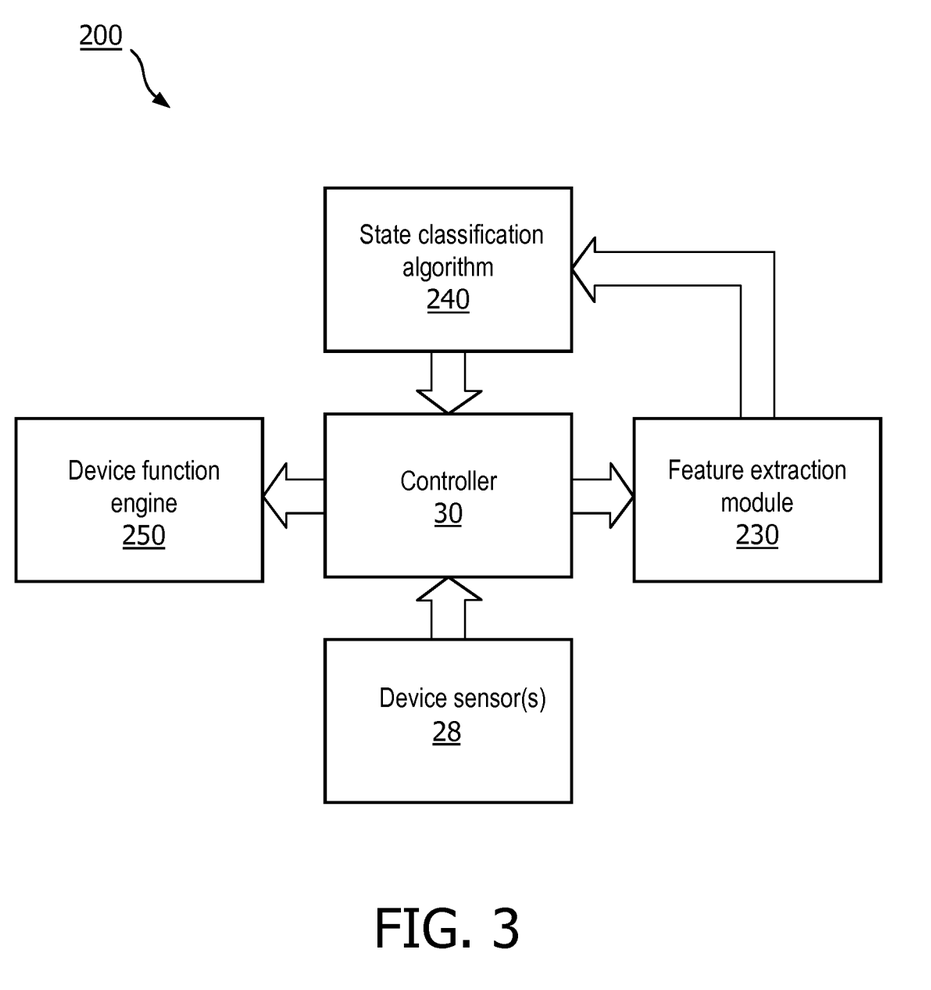
FIG. 3 is a schematic representation of a personal care system, in accordance with an embodiment.

Referring to FIG. 3, in one embodiment, is a system 200 for controlling powered personal care device 10 based on a status of a portion of a user's body. The system 200 is an embodiment of personal care device 10, such as for example, a powered oral care device embodiment disclosed or otherwise envisioned herein. According to another embodiment, system 200 can be implemented in two or more devices. For example, one or more of the modules or components of system 200 can be implemented in a remote device such as a smartphone, tablet, wearable device, computer, or other computer.

The system 200 includes controller 30 and one or more sensors 28 configured to obtain information about a user's body and generate sensor data related to the user's body or movement characteristics of the user's body. Controller 30 is configured to receive sensor data from one or more sensors 28.

The system 200 also includes a feature extraction module 230 and state classification algorithm module 240. The feature extraction module 230 is configured to receive a sensor signal from the controller 30 based on the sensor data received at the controller. According to an embodiment, the feature extraction module 230 is a component of controller 30. The feature extraction module 230 is configured, designed, or programmed to extract one or more features from a feature vector from the sensor data using signal processing. These features provide information corresponding to distinct states and/or levels that can be used for classification. In an embodiment, body states and/or levels can be pre-defined according to standards or individual users. Using the one or more extracted features, state classification algorithm module 240 determines a discrete state or a level within a continuous range of states or levels and transmits such state or level to the controller 30.

System 200 also includes a device function engine 250 configured to adjust how the personal care device 10 is operated. In other words, device function engine 250 is configured to receive or detect information about a user's body and/or level and provide instructions to electronically adjust the behavior of personal care device 10.

In the case of powered personal care devices, control signals may turn the device on or off, change the operating mode or operating intensity. For example, if the powered personal care device is an oral care device such as an electric toothbrush or water flossing device, upon detecting that a user's mouth is open or opening, one or more control signals can be sent automatically to adjust the operating intensity. For example, reducing the operating intensity if the mouth is detected to be opening may reduce the likelihood of substances escaping the mouth in the environment due to the powered operation of the head member.

The term "status" as used herein may represent an absolute status (for example, open or closed) or a relative status (for example, a change in status compared to some reference at a previous time). In an example embodiment, upon detecting a status of a user's oral cavity, device function engine 250 may additionally or alternatively be designed to provide feedback to the user or a third party. In the case of powered personal care devices, suitable feedback may be provided via haptic feedback, LED embedded within the device or any suitable mechanism at the user's disposal while operating the powered personal care device.

In the case of personal care devices with imaging sensors 28a, the device function engine 250 may be designed that upon detecting that a certain state of the user's body (i.e. body temperature, skin moisture content, or other condition), device function engine 250 sends control signals to the imaging sensors 28a, for example, via a control unit, instructing it to capture images or take certain other actions. For example, if the imaging sensors are to be used to obtain images of the inside of a user's mouth, upon detecting that a user's mouth is open, one or more control signals can be sent automatically to enable the imaging sensors to capture images of the user's oral cavity; alternatively, if the user's mouth is closed, the imaging sensors can be disabled from capturing images. This ensures that images obtained from the imaging sensors only contain information of a region of interest, but also ensures that the device operates more efficiently and autonomously, thereby preserving energy.

In an example embodiment, system 200 can be used to provide guidance to a user to an optimal positioning of an oral care device for maximum exposure of the user's oral cavity.

Figure 4:
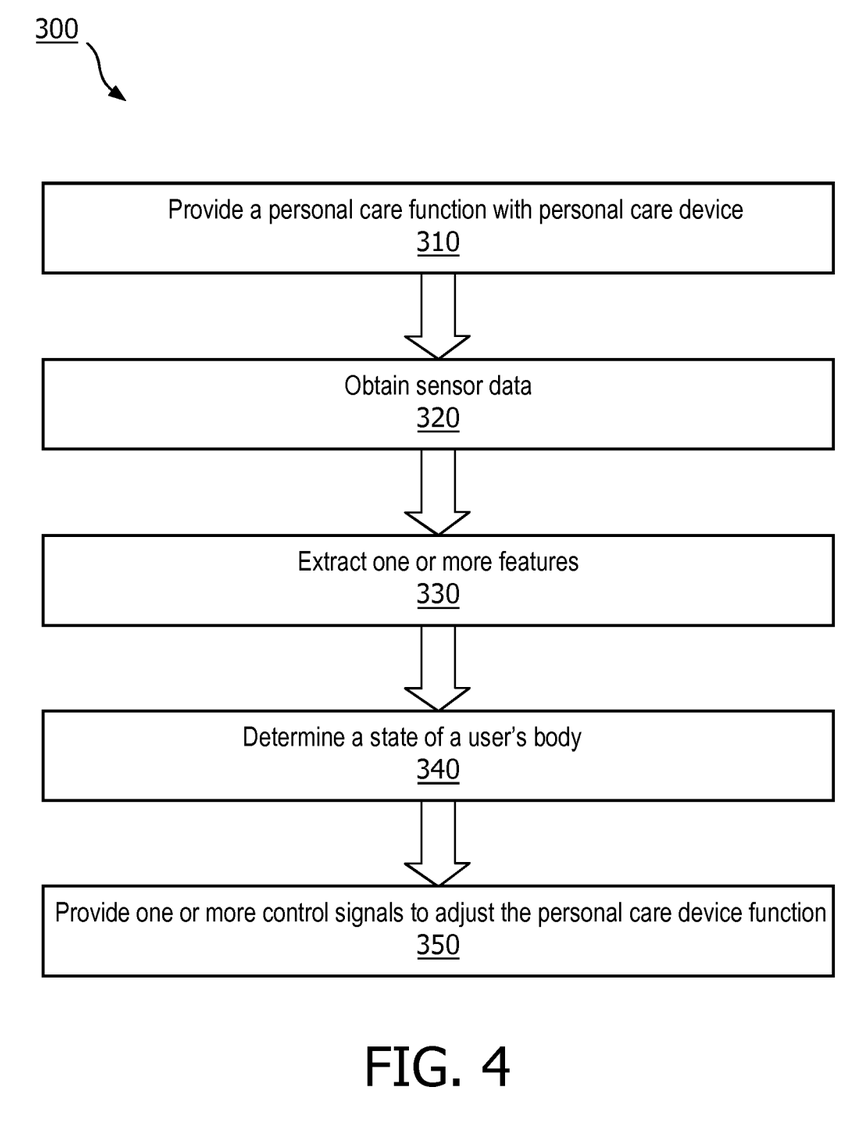
FIG. 4 is a flowchart of a method for controlling a personal care device, in accordance with an embodiment.

Referring to FIG. 4, in an embodiment, is a flowchart of a method 300 for controlling a powered personal care device based on a status of a user's body. At step 310, a powered personal care device 10 is used to provide one or more personal care functions. Personal care device 10 can be any of the devices described or otherwise envisioned herein. In an example embodiment, the powered personal care device 10 is an oral care device that is to be operated in a user's oral cavity during an oral care session or according to teledentistry practices. The personal care function can embody any characteristic of the personal care device, for example, one or more operating modes (e.g., brushing modes) which may set forth operating frequencies, amplitude, and/or patterns, powered/non-powered states (or ON/OFF condition), light source activation modes, positioning modes, imaging modes, operating intensity modes, or any other suitable characteristic.

At step 320 of the method, sensor data from one or more sensors 28 is obtained while the user operates the powered personal care device 10. The information can additionally or alternatively include movement characteristics of the device or the user's body in an embodiment. The sensor data may be communicated to the controller 30 and/or the feature extraction module 230. The sensor data may be used immediately or may be stored, for example in memory 34, or otherwise queued for later analysis. Alternatively, the sensor data are stored remotely from the device in a remote server, database, or other storage unit.

At step 330 of the method, the feature extraction module 230 extracts one or more features from a sensor signal generated by controller 30 based on the sensor data. The feature extraction module 230 may extract one or more features depending on the sensors present in the device or system. At step 340 of the method, the state classification algorithm module 240 identifies a state or level of a portion of the user's body.

For example, state classification could be used in an oral care device to determine if a user's mouth is in an open state or a closed state. A single sensor modality is sufficient to detect two discrete mouth aperture states, open or closed. Depending on the signal resolution afforded by the chosen sensors, a mouth aperture may be defined to fall into discrete states (open or closed) or defined to fall in a continuous range of aperture levels by selection of a suitable normalization function. In an example embodiment including a single optical proximity sensor, the two discrete mouth aperture states, open or closed, can be detected using the following threshold-based equation:

$$a = \frac{f(s_1) * w(s_1)}{r(s_1)}$$

$$\text{where } f(s_1) = \begin{cases} 1, & s_1 \geq \text{Threshold} \\ 0, & s_1 \leq \text{Threshold} \end{cases}$$

$w(s_1)=1$ and $r(s_1)=1$ for input $s_1$ from proximity sensors. In this example embodiment, $f(s_1)$ is a function that extracts features from sensor 1, $w(s_1)$ is a function that assigns a weight to the same sensor input, and $r(s_1)$ is a normalization function that ensures that the corresponding aperture level falls in a specific range. The weighting function is employed to assign a weight that defines the contribution each sensor output has in the determination of the aperture. The feature extraction module 230 can include the extraction function and the state classification algorithm module 240 can include the weighting and normalization functions in an embodiment.

Figure 5:
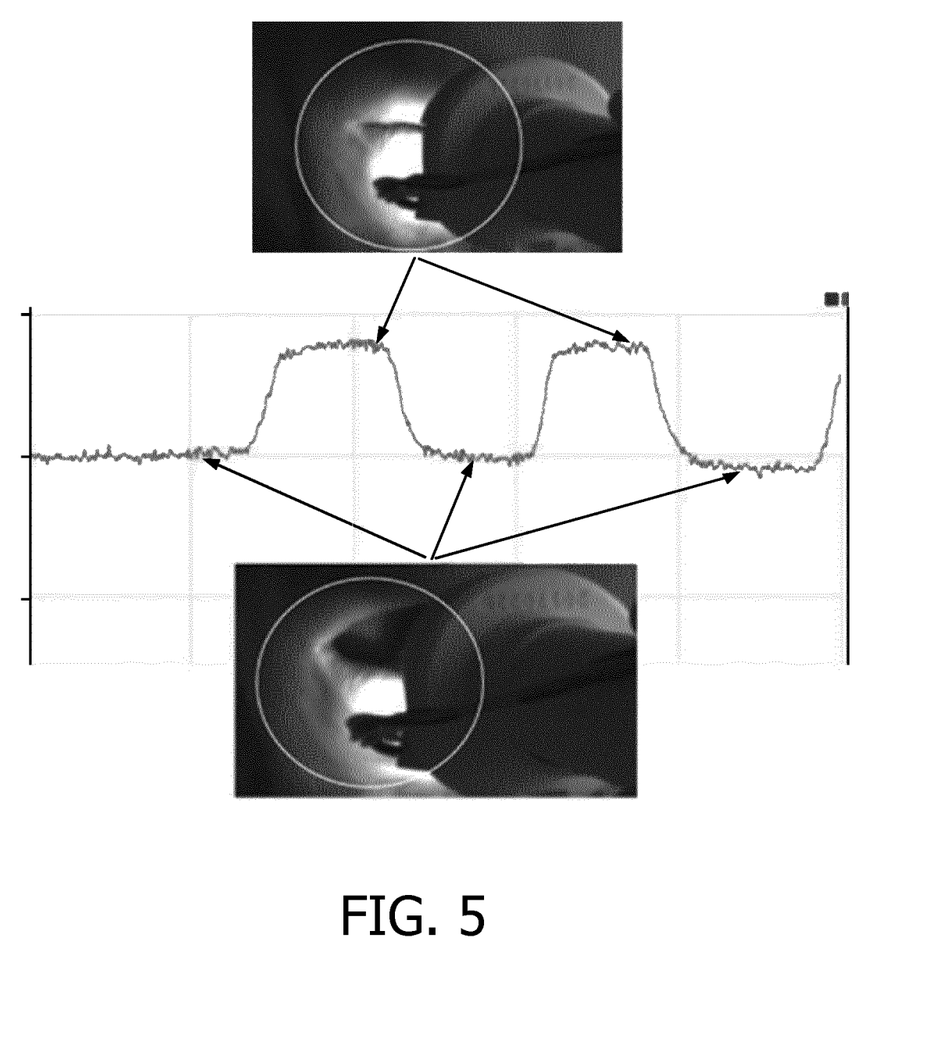
FIG. 5 is a representation of a sensor signal related to discrete states where a user's mouth is open/closed, in accordance with an embodiment.

FIG. 5 shows an example of sensor output from a single optical proximity sensor over a period of time. A suitable algorithm such as is described above can be implemented to extract features from the sensor output. When viewing the output from left to right, there are five time intervals that can be related to discrete states where a user's mouth is open or closed. From left to right, the first, third, and fifth time intervals can be related to a mouth open state, while the second and fourth time intervals can be related to a mouth closed state. The signals represent measured light intensities based on light reflected from a user's mouth. The signals in the first, third, and fifth time intervals are lower since less light is reflected from the mouth while the signals in the second and fourth time intervals are higher since more light is reflected from the mouth. The personal care device or a component of the system, such as the controller relates the output generated by the one or more sensors to open or closed states of the oral cavity by any suitable mathematical functions or algorithms.

Although in the described embodiment, the device sensor includes a single proximity sensor, it will be understood that in alternative embodiments the device sensor includes any other suitable sensors. For example, in the system described above, personal care device 10 can include one or more sensors 28, which in this representative embodiment are pressure sensors. These sensors 28 are configured to sense pressure from a user's top lip, bottom lip, or both top and bottom lips. If pressure is detected from a user's top and bottom lips, it can be inferred that the user's mouth is closed. Similarly, if pressure is detected from a user's top lip or bottom lip but not both, it can be inferred that the user's mouth is at least partially open.

According to another embodiment, pressure sensors can be used to detect whether a user's mouth is opening or closing. For example, based on increasing or otherwise changing pressures detected from a user's top and bottom lips, it can be inferred that the user's mouth is closing. Similarly, based on decreasing or otherwise changing pressures detected from a user's top and bottom lips, it can be inferred that the user's mouth is opening. Using one or more optical proximity sensors, it can be inferred that a user's mouth is opening or closing based on decreasing or increasing signals, respectively, as discussed above.

According to an embodiment, the extracted features can be used immediately or stored in a database, for example, in memory 34, or accessed via an external memory or controller 30. The systems and methods described herein can include a machine learning classifier to create a classification model that predicts states and/or levels based on the extracted features. According to an embodiment, a training database can be created and the machine learning classifier can be used with the training database to create a predictive model. Examples of suitable machine learning algorithms include support vector machines, K-nearest neighbors, logistic regression, and/or decision trees, among many other possible machine learning algorithms. In an embodiment where the extracted features are used immediately, the predictive model can be used to identify regions of the feature space that should be associated with each state or level.

According to an embodiment, training the personal care device to identify a status of a particular state or level includes one or more steps described herein, which may be repeated numerous times, including while the personal care device is in use. In an example training phase, the personal care device obtains sensor data for at least part of one personal care session when the personal care device is in use. According to an embodiment, the more training sessions that are analyzed, the more training data is used to train the classifier, and the better the classifier is able to identify states or levels. Additionally, the extraction module extracts a plurality of features from the sensor data. According to an embodiment, discriminant features are extracted from the sensor data for every operating session recorded by the device. The choice of features depends on the sensors present in the device.

According to an embodiment, if other sensors are present in the device, other discriminant features may be extracted. Among these features are, for example: proximity patterns during the operating session, if the device has a proximity sensor such as a capacitive sensor and/or facial features commonly used for face recognition if the device contains a camera.

At step 350 of the method, depending on the detected or determined state, one or more control signals are provided to adjust one or more personal care functions of the personal care device. In an embodiment, one or more control signals are sent to a processing unit which will then send control signals to personal care device 10. In an example embodiment, the control signals will instruct the personal care device to deactivate or change a suitable function. Referring to the embodiment depicted in FIG. 5, advantageously, the inventive systems and methods described herein are configured to infer that a user's mouth is open or opening during the first signal set and, when the different signals are detected in the second signal set, that the user's mouth is closed or closing. Based on this determination while the user is using the device, the system can automatically adjust a personal care function to account for the changed status or state of the user's oral cavity.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. An oral care system, comprising:
at least one sensor configured to obtain sensor data comprising information about an oral cavity of a user;
a controller comprising a feature extraction module and a machine learning classifier, the feature extraction module configured to extract one or more features from the obtained sensor data, and the machine learning classifier configured to determine a status of the oral cavity of the user based on the extracted one or more features, wherein the status of the oral cavity comprises identification of when the user's mouth is open, closed, opening or closing; and
an oral care device configured to i) provide an oral care function and ii) receive one or more control signals to adjust the oral care function based on the determined status of the oral care of the user.

2. The oral care system of claim 1, further comprising a device function engine configured to receive a control signal from the controller and transmit one or more control signals to the oral care device to adjust the oral care function.

3. The oral care system of claim 1, wherein the at least one sensor comprises an imaging sensor.

4. The oral care system of claim 1, wherein the at least one sensor is comprises an optical proximity sensor.

5. The oral care system of claim 1, wherein the status of the oral cavity of the user is determined by assigning a weight to the sensor data from each of the one or more sensors.

6. The oral care system of claim 5, wherein the status of the oral cavity of the user is determined by applying a normalization function to the weighted sensor data from each of the one or more sensors.

7. The oral care system of claim 1, wherein the system is configured to provide feedback to the user or a third party based on the determined state of the oral cavity.

8. The oral care system of claim 1, wherein the oral care device function comprises an operating intensity.

9. The oral care system of claim 1, wherein the oral care function comprises an operating mode.

10. The oral care system of claim 1, wherein the oral care function is a powered or non-powered state.

11. The oral care system of claim 1, wherein: the oral care device further comprises an imaging device; the one or more sensors comprise an imaging sensor; and the oral care function comprises capturing an image of the oral cavity.

12. A method for controlling an oral care device based on a status of an oral cavity of a user, the method comprising:
providing an oral care function with an oral care device;

obtaining, by one or more sensors associated with the oral care device, sensor data comprising information about the oral cavity of the user;

extracting, by a feature extraction module, one or more features from the obtained sensor data;

determining, using a trained machine learning classifier, a status of the oral cavity of the user based on the extracted one or more features, wherein the status of the oral cavity comprises identification of when the user's mouth is open, closed, opening, or closing; and based on the determined status of the oral cavity of the user, transmitting one or more control signals to adjust the oral care function provided by the oral care device.

13. The method of claim 12, further comprising training a classifier using the extracted one or more features to create a classification model adapted to predict the status of the oral cavity of the user prior to the determining.

14. The method of claim 12, wherein the determining the status of the oral cavity of the user comprises assigning a weight to the sensor data from each of the one or more sensors.

15. The method of claim 14, wherein the determining the status of the oral cavity of the user further comprises applying a normalization function to the weighted sensor data from each of the one or more sensors.

16. The method of claim 12, further comprising providing feedback to the user or a third party based on the determined status of the oral cavity of the user.

17. The method of claim 12, wherein the oral care function comprises an operating intensity.

18. The method of claim 12, wherein the oral care function is an operating mode.

19. The method of claim 12, wherein the oral care function is a powered state or non-powered state.

20. The method of claim 12, wherein: the oral care device further comprises an imaging device and the one or more sensors comprise an imaging sensor; and the oral care function comprises capturing an image of the oral cavity of the user.

* * * * *